Figure 1:
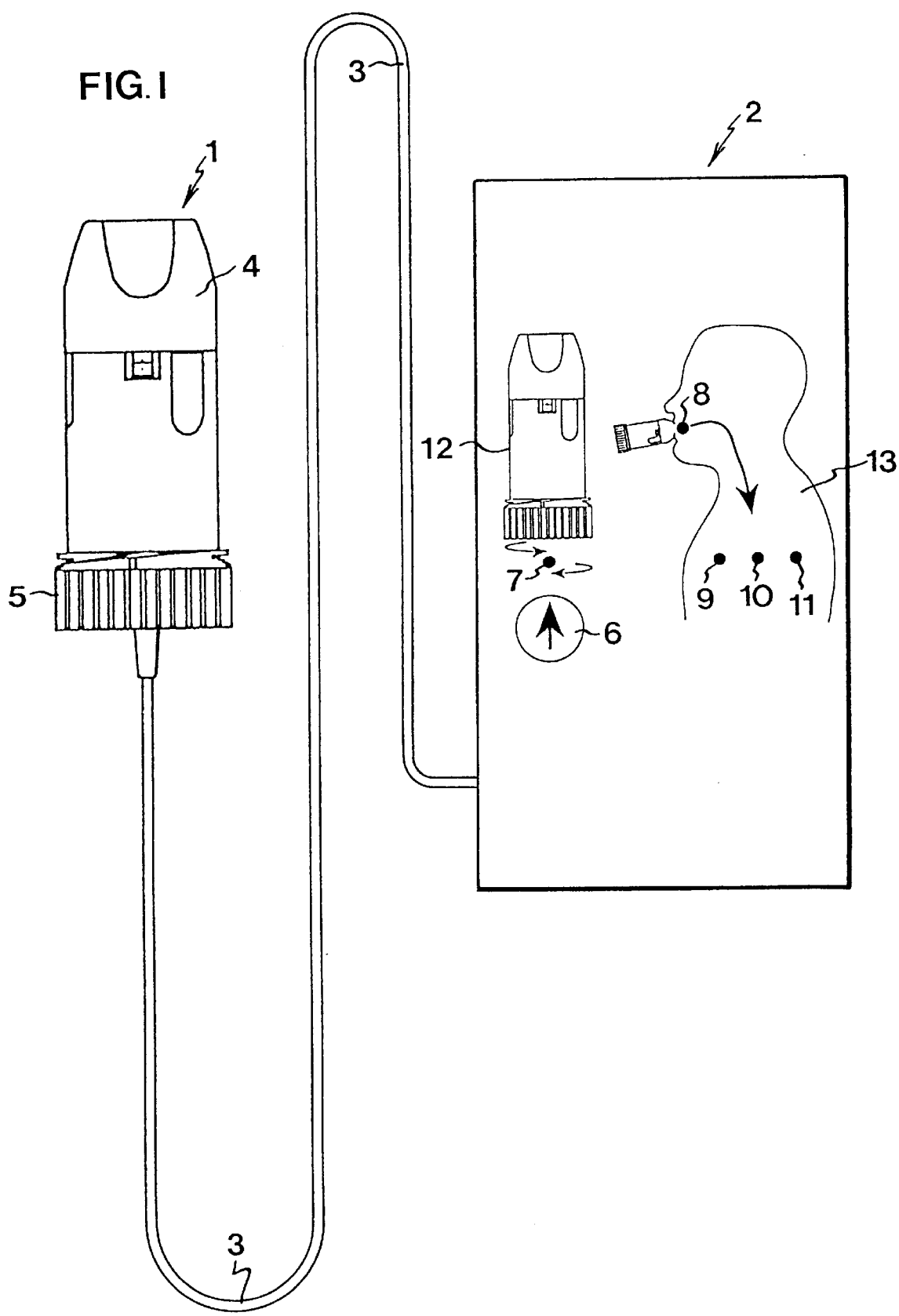

United States Patent
Marnfeldt et al.

[11] Patent Number: 5,839,429
[45] Date of Patent: Nov. 24, 1998

[54] METHOD AND APPARATUS IN CONNECTION WITH AN INHALER

[75] Inventors: Nils Göran Marnfeldt, Blentarp; Johan Mats Bertil Waldeck, Sandby, both of Sweden

[73] Assignee: Astra Aktiebolag, Sodertalje, Sweden

[21] Appl. No.: 915,121

[22] Filed: Aug. 20, 1997

Related U.S. Application Data

[63] Continuation of Ser. No. 436,434, filed as PCT/SE95/00315 Mar. 24, 1995 published as WO95/26212 Oct. 5, 1995, abandoned.

[30] Foreign Application Priority Data

Mar. 25, 1994 [SE] Sweden ............................. 9401020-4

[51] Int. Cl.[6] .................................................. A61M 11/00
[52] U.S. Cl. ............................. 128/200.14; 128/203.15; 128/204.23; 128/205.23
[58] Field of Search ................... 128/200.14, 200.23, 128/203.12, 204.23, 205.23, 203.15

[56] References Cited

U.S. PATENT DOCUMENTS

| | | | |
|---|---|---|---|
| 3,809,294 | 5/1974 | Torgeson | 128/203.15 |
| 3,897,779 | 8/1975 | Hansen | 128/203.15 |
| 4,495,944 | 1/1985 | Brisson et al. | 128/725 |
| 4,984,158 | 1/1991 | Hillsman | 128/725 |
| 5,019,974 | 5/1991 | Beckers | 364/413.02 |
| 5,152,456 | 10/1992 | Ross et al. | 128/200.16 |
| 5,167,506 | 12/1992 | Killis et al. | 128/725 |
| 5,284,133 | 2/1994 | Burns et al. | 128/203.15 |
| 5,331,953 | 7/1994 | Andersson et al. | 128/200.14 |

FOREIGN PATENT DOCUMENTS

| | | |
|---|---|---|
| 0387222A1 | 9/1990 | European Pat. Off. . |
| 2164569 | 3/1986 | United Kingdom ............. 128/203.12 |
| WO 92/15353 | 9/1992 | WIPO . |
| WO 93/12823 | 7/1993 | WIPO . |
| WO93/12823 | 7/1993 | WIPO . |

*Primary Examiner*—Aaron J. Lewis
*Attorney, Agent, or Firm*—Fish & Richardson P.C.

[57] ABSTRACT

An apparatus for training a person to use an inhaler comprises such an inhaler connected to a processing device. The inhaler comprises means for detecting when the inhaler is activated for making a dose of a drug available for inhalation and means for detecting the inhalation flow through the inhaler. The processing device comprises means for indicating to the patient how the inhaler is to be activated in order to make a dose available and means for urging the patient to perform such an activation. The latter means are activated when the apparatus is turned on and deactivated when a proper activation of the inhaler is detected. The processing device further comprises means for urging the patient to inhale through the inhaler. These means are activated when a proper activation of the inhaler is detected and deactivated when an inhalation flow is detected. The measured inhalation flow is indicated by indication means on the processing device.

A method for training a person to use an inhaler is also disclosed.

3 Claims, 3 Drawing Sheets

METHOD AND APPARATUS IN CONNECTION WITH AN INHALER

This is a continuation of application Ser. No. 08/436,434, filed as PCT/SE95/00315 Mar. 24, 1995 published as WO95/26212 Oct. 5, 1995, now abandoned.

The present invention relates to a method and an apparatus for training a patient to use an inhaler.

In order that a breath-activated dry powder inhaler should release a dose of a drug contained therein and the dose should reach far enough into the lungs of the patient inhaling through the inhaler, the inhalation flow must reach a certain critical limit. Since the patient cannot tell the difference between an inhalation containing a dose of a drug and an inhalation not containing any dose of the drug, it is difficult for him to know whether he has actually received his dose or not. Therefore, it is important that the patient learns how to use the inhaler correctly right from the beginning and also that he and his doctor can check his use of the inhaler occasionally.

Today, there does not exist any suitable apparatus for training and checking the use of a breath-activated dry powder inhaler. Sometimes, an inhaler is connected to equipment for performing pulmonary function tests (PFT). The inhalation flow is displayed as a function of time on a screen, and a doctor assesses whether the inhalation is correctly performed. However, the PFT equipment is very expensive and may thus be used only at hospitals and the like. Furthermore, a person must be present to instruct the patient, operate the equipment and assess the result.

Accordingly, a first object of the present invention is to provide an apparatus for training a patient to use an inhaler correctly, this apparatus being inexpensive and easy to use and dispensing with the need of any assistance from trained personnel.

A second object of the present invention is to provide a method for training a patient to use an inhaler correctly.

These objects are achieved by an apparatus and a method having the features recited in the appended claims.

The apparatus according to the invention provides interactive directions for the correct use of an inhaler. The apparatus can be used by everyone without any assistance, since the use of it is self-explanatory. Each step to be performed is indicated to the patient in turn, and the inhalation flow is not measured until a correct activation of the inhaler for making a dose available has been detected. The apparatus comprises an inhaler which is similar to the one the patient normally uses or will use so that the training is realistically performed.

Figure 2:
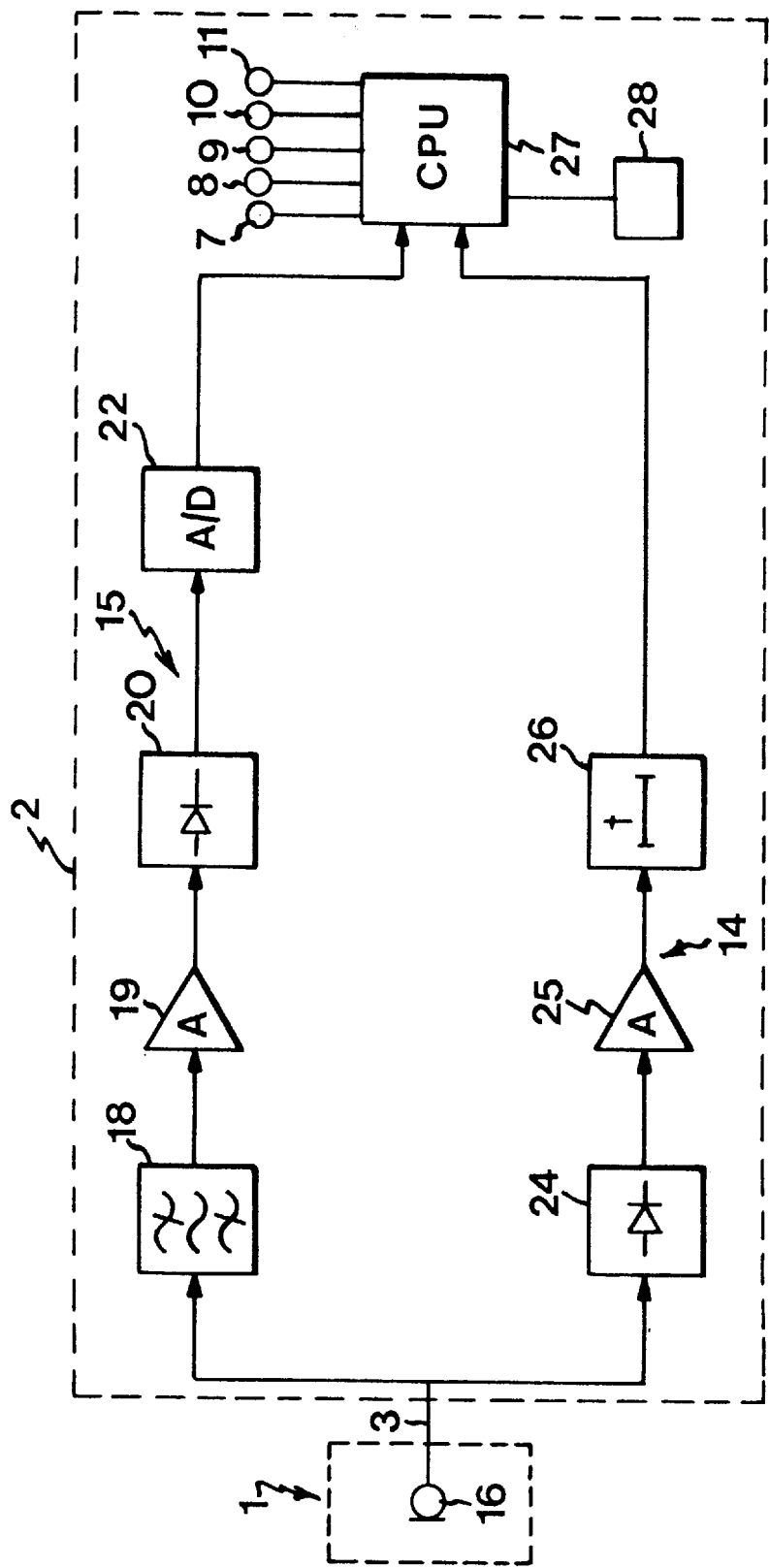
Figure 3:
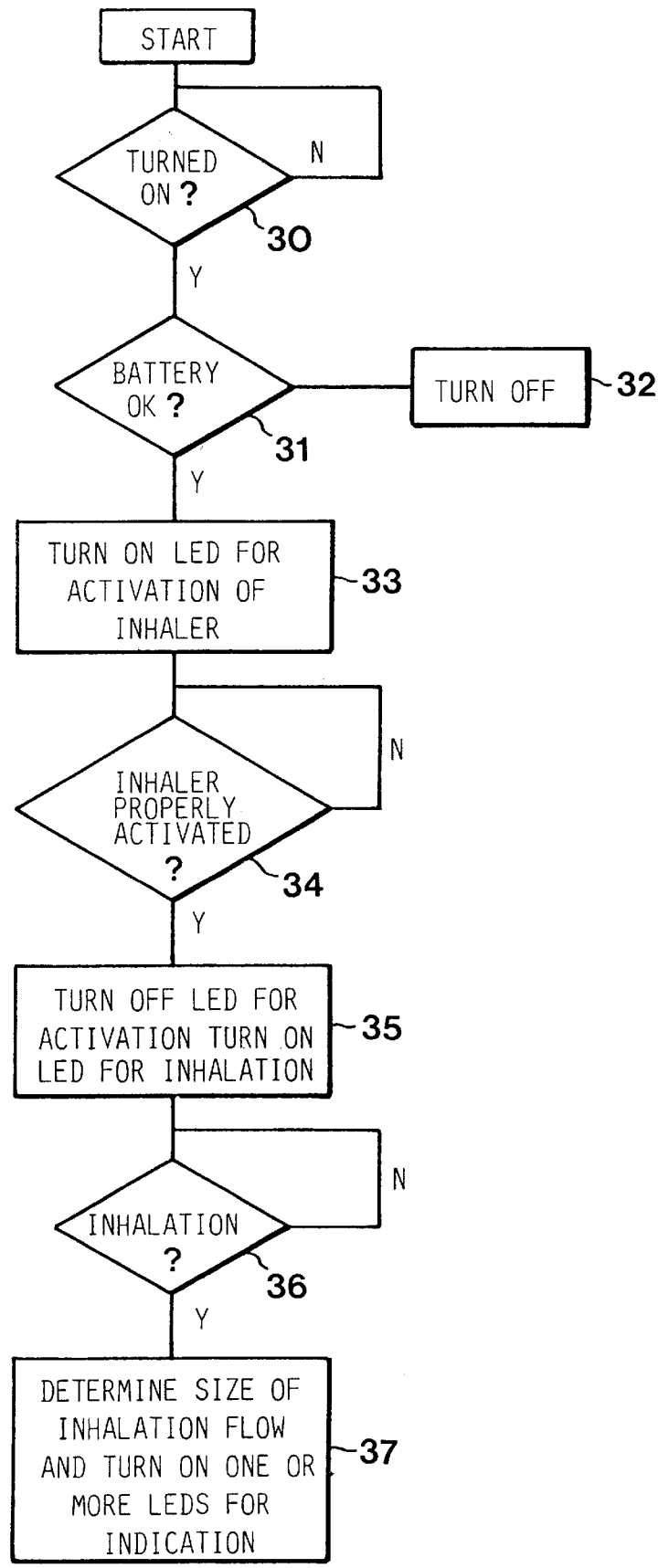

One embodiment of the apparatus and the method according to the present invention will now be described in more detail with reference to the accompanying drawings, in which FIG. 1 is a schematic view showing an embodiment of an apparatus according to the present invention;

FIG. 2 is a block diagram, showing electronical components of the apparatus in FIG. 1; and FIG. 3 is a flow diagram, showing the operation of the apparatus in FIG. 1.

As appears from FIG. 1, a training apparatus according to the present invention substantially consists of an inhaler 1 and a box-shaped portable processing device 2, to which the inhaler is connected by a cable 3.

The inhaler 1 is a TURBUHALER® inhaler, the substance container of which is empty or holds an ineffective substance in the form of a dry powder. It has a replaceable mouthpiece 4 made of e.g. plastics, and a gripping ring 5, which is to be turned in order to make a dose available for inhalation.

On its upper side, the processing device 2 is provided with a switch 6 for turning on the apparatus, and a plurality of light-emitting diodes 7–11 for indicating the different steps to be taken as well as the inhalation flow. Furthermore, there is a picture 12 of a TURBUHALER®inhaler with two arrows indicating how the inhaler is to be operated in order to make a dose available, and a picture 13 indicating inhalation through the inhaler.

Furthermore, the training apparatus comprises means for detecting the activation of the inhaler in order to make a dose available for inhalation and for detecting the inhalation flow. Such means may be of the kind disclosed in EP 387 222 and will be briefly described in the following with reference to FIG. 2.

A microphone 16 is arranged in the inhaler 1 close to an inhalation channel (not shown) therein. The microphone 16 is connected to processing means in the processing device 2 by the cable 3.

The microphone 16 detects the characteristic click sound created when the gripping ring 5 is turned, as well as the sound of the airflow at an inhalation. These signals are transferred to the processing device 2 via the cable 3.

A first branch 14 of the processing device, which is adapted to process the click sound, comprises a rectifier 24 which rectifies the click sound signal. The rectifier 24 is connected to an amplifier 25, which amplifies the rectified signal to about 1 V. The amplified signal is input into a puls stretcher 26, which stretches the amplified signal to a signal which can be recorded as a valid activation of the inhaler in a processor 27.

A second branch 15 of the processing device, which is adapted to process the inhalation flow signal, comprises a band pass filter 18, which passes a signal within a limited frequency range. The filtered signal is input into an amplifier 19, which amplifies the signal to about 1 V. The amplified signal is rectified and low-pass filtered in a detector 20 so that the envelope of the signal is obtained. Then, the envelope signal, which represents the momentary inhalation flow, is A/D-converted in a A/D-converter 22 before being input into the processor 27. In addition to the inputs from the first and second branches 14, 15, the processor 27 have outputs to the LED's 7–11 on the upper side.

The operation of the apparatus shown in FIGS. 1 and 2 will now be described with reference to the flow diagram in FIG. 3.

When the processor 27 detects (step 30) that the training apparatus has been turned on by the pressing of the switch 6, it turns on all the LED's 7–11 for a short while and measures the battery voltage to check whether it is sufficient for performing one or more training cycles (step 31). If the battery is discharged, the processor 27 turns off the apparatus (step 32), whereas if the battery is sufficiently charged, the processor 27 turns on the LED 7 to indicate that the gripping ring 5 is to be turned in order to make a dose available (step 33). When the processor receives a signal which represents a proper turning of the gripping ring 5 as detected by the microphone 16 (step 34), it turns off the LED 7 and turns on the LED 8 to urge the patient to inhale through the inhaler (step 35). When the patient inhales through the inhaler, the sound of the inhalation flow is detected by the microphone (step 36). The signal from the microphone 16 is processed in the second branch 15 and input into the processor 27, which determines the size of the inhalation flow (step 37) and turns on one or more of the LEDs 9–11, each LED corresponding to a different inhalation flow achieved. As an example, the first LED 9 may be turned on at an inhalation flow of 30 l/min, the second LED 10 at 40 l/min and the third LED 11 at 60 l/min.

The levels at which the different LEDs are turned on may be changed without opening the processing device 2. To this end, the processing device comprises a calibration switch arranged inside its cover. The calibration switch is operable from the outside of the cover by means of a magnetic element. To transfer the apparatus to a calibration mode both the calibration switch and the switch 6 must be activated at the same time. When the calibration mode is entered, the processor 27 turns on the first LED 9. Then, the turning-on level of the first LED 9 can be set by feeding a flow corresponding to the desired turning-on level through the inhaler and, at the same time, pressing the switch 6. When the level of the first LED 9 has been set, the processor turns off the first LED 9 and turns on the second LED 10, the level of which may now be set. Finally, the level of the third LED 11 may be set in the same way.

The calibrated turning-on levels of the LEDs are stored in a non-volatile memory 28, from which they are fetched when the processor 27 determines which LED(s) to turn on for indicating the inhalation flow.

Since it is important that the inhaler is held in a substantially vertical position, at least not deviating more than 45 degrees from the vertical, when the inhaler is activated for making a dose available, the inhaler may, as a further feature, be provided with a position transducer. The position transducer may be connected to the processing device 2 via the cable 3. In this case, the processing device 2 need to detect both the click sound created when the inhaler is activated for making a dose available and a correct position of the inhaler during the activation, in order that it shall turn on the LED 8 for urging the patient to inhale through the inhaler.

In the embodiment described above a microphone is used for the detection of the activation of the inhaler and for the detection of the inhalation flow. Alternatively, other means, such as a pressure transducer, can be used.

The method and the apparatus according to the present invention can be used to train a person to use any kind of inhaler, where first the dose is made available for inhalation and then the inhalation is performed. For instance, the inhaler may be a breath-activated dry powder inhaler, in particular a TURBUHALER® inhaler.

We claim:

1. A training device for training a patient to use a breath-activated dry powder inhaler correctly, the training device comprising:

a breath-activated dry powder inhaler that is constructed to move a dose of powdered medicament into position for inhalation when activated by a patient, and to subsequently dispense said dose when a patient applies a sufficient inspiratory flow to said inhaler;

an activation signal constructed to indicate to a patient an instruction to activate the inhaler;

an activation sensor constructed to detect when a patient has activated the inhaler;

an inhalation signal constructed to indicate to a patient, after detection of inhaler activation, an instruction to inhale through the inhaler;

an inhalation flow sensor constructed to measure the inspiratory flow rate through the inhaler; and a flow signal to indicate to a patient the inspiratory flow applied, wherein each of said activation sensor and said inhalation sensor comprises a microphone, wherein said activation sensor further comprises a position transducer and said activation signal comprises an indicator for indicating whether the inhaler is held in a correct position during activation.

2. A training device for training a patient to use a breath-activated dry powder inhaler correctly, the training device comprising:

a breath-activated dry powder inhaler that is constructed to move a dose of powdered medicament into position for inhalation when activated by a patient, and to dispense said dose when a patient applies a sufficient inspiratory flow to said inhaler;

an activation signal constructed to indicate to a patient an instruction to activate the inhaler;

an activation sensor constructed to detect when a patient has activated the inhaler, said activation sensor comprising a position transducer;

an inhalation signal constructed to indicate to a patient an instruction to inhale through the inhaler, said activation signal comprising an indicator for indicating whether the inhaler is held in a correct position during activation;

an inhalation flow sensor constructed to measure the inspiratory flow rate through the inhaler; and a flow signal to indicate to a patient the inspiratory flow applied.

3. The device of claim 2, wherein each of said activation sensor and said inhalation sensor comprises a microphone.

* * * * *